United States Patent
Jackwood et al.

(10) Patent No.: US 10,898,307 B2
(45) Date of Patent: Jan. 26, 2021

(54) SYSTEM AND METHOD FOR FOWL VACCINATION

(71) Applicant: The University of Georgia Research Foundation, Inc, Athens, GA (US)

(72) Inventors: Mark W Jackwood, Watkinsville, GA (US); Brian Jordan, Watkinsville, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 182 days.

(21) Appl. No.: 15/538,630

(22) PCT Filed: Dec. 21, 2015

(86) PCT No.: PCT/US2015/067223
§ 371 (c)(1),
(2) Date: Jun. 21, 2017

(87) PCT Pub. No.: WO2016/106254
PCT Pub. Date: Jun. 30, 2016

(65) Prior Publication Data
US 2017/0360540 A1   Dec. 21, 2017

Related U.S. Application Data

(60) Provisional application No. 62/095,495, filed on Dec. 22, 2014.

(51) Int. Cl.
*A61D 7/00* (2006.01)
*A61D 1/02* (2006.01)
*A61M 11/00* (2006.01)

(52) U.S. Cl.
CPC ............... *A61D 7/00* (2013.01); *A61D 1/025* (2013.01); *A61M 11/00* (2013.01); *A61M 2250/00* (2013.01)

(58) Field of Classification Search
CPC ....... A61D 7/00; A61M 11/00; A61M 11/006; A61M 11/02; A61M 11/04
See application file for complete search history.

(56) References Cited

U.S. PATENT DOCUMENTS 2,767,117 A * 10/1956 Crawley ................ A61K 39/17
424/214.1
2,910,407 A * 10/1959 Hitchner ................ A61D 1/025
424/229.1

(Continued)

FOREIGN PATENT DOCUMENTS

CA   2427907 A1   7/2004
CN   1671427 A    9/2005
(Continued)

OTHER PUBLICATIONS

"Vaccination", Poultry Hub, archived Aug. 8, 2012, <http://www.poultryhub.org/health/health-management/vaccination/> (Year: 2012).*
(Continued)

*Primary Examiner* — Michael H Wang
(74) *Attorney, Agent, or Firm* — Thomas | Horstemeyer, LLP

(57) ABSTRACT

A method, apparatus and system for delivery of live or attenuated viral and bacterial vaccines to fowl are described.

14 Claims, 3 Drawing Sheets

(56) References Cited

U.S. PATENT DOCUMENTS

| | | | |
|---|---|---|---|
| 3,465,717 A | 9/1969 | Hein | |
| 4,316,464 A * | 2/1982 | Peterson | A61D 7/00 604/24 |
| 4,449,968 A * | 5/1984 | Peterson | A61D 1/025 604/24 |
| 4,674,490 A * | 6/1987 | Frankel | A61D 1/025 119/678 |
| 4,850,997 A * | 7/1989 | DuBose | A61D 1/025 604/289 |
| 4,863,443 A * | 9/1989 | Hornung | A61D 1/025 604/500 |
| 5,068,104 A * | 11/1991 | Bhogal | A61K 39/012 424/193.1 |
| 5,630,379 A * | 5/1997 | Gerk | A01K 13/001 119/667 |
| 6,230,660 B1 * | 5/2001 | Greeson | A01K 13/003 119/656 |
| 6,541,001 B1 | 4/2003 | Gallili et al. | |
| 6,910,446 B2 * | 6/2005 | Johnston, Jr. | A01K 45/00 119/651 |
| 7,258,079 B2 * | 8/2007 | Foster | A01K 13/00 119/174 |
| 9,827,305 B2 * | 11/2017 | Qiao | A61K 39/12 |
| 2003/0207019 A1 | 11/2003 | Shekalim et al. | |
| 2004/0144873 A1 | 7/2004 | Johnston, Jr. | |
| 2006/0110406 A1 | 5/2006 | Kemble et al. | |
| 2008/0195064 A1 * | 8/2008 | Correa | A61D 1/025 604/289 |
| 2011/0217322 A1 * | 9/2011 | Purswell | A61D 1/025 424/184.1 |
| 2013/0135407 A1 | 5/2013 | Abe et al. | |
| 2015/0174321 A1 * | 6/2015 | Cohen | A61D 1/025 604/506 |

FOREIGN PATENT DOCUMENTS

| | | |
|---|---|---|
| CN | 101112700 A | 1/2008 |
| CN | 103129175 | 6/2013 |
| JP | 58105310 | 7/1983 |
| JP | S58105310 | 7/1983 |
| RU | 2277905 C2 | 6/2006 |

OTHER PUBLICATIONS

International Search Report for PCT/US2015/067223.
Written Opinion of the International Searching Authority, International Application PCT/US2015/067223.
Machine translation of CN 101112700A.
Machine translation of CN 103129175.
Machine translation of RU 2277905.
Machine translation of CN 1671427.

\* cited by examiner

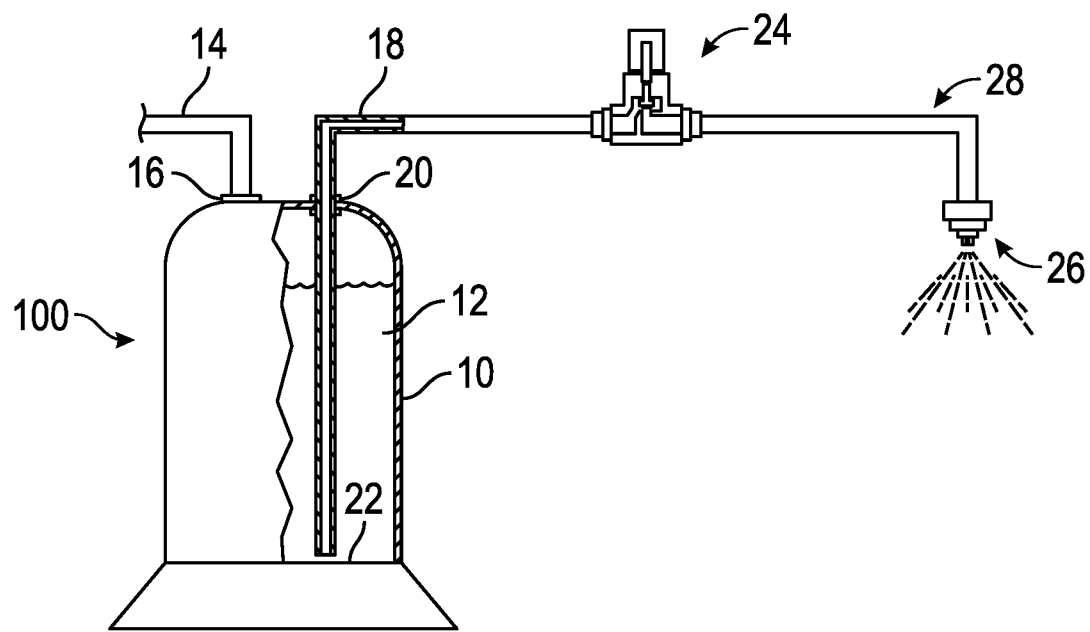
FIG. 1
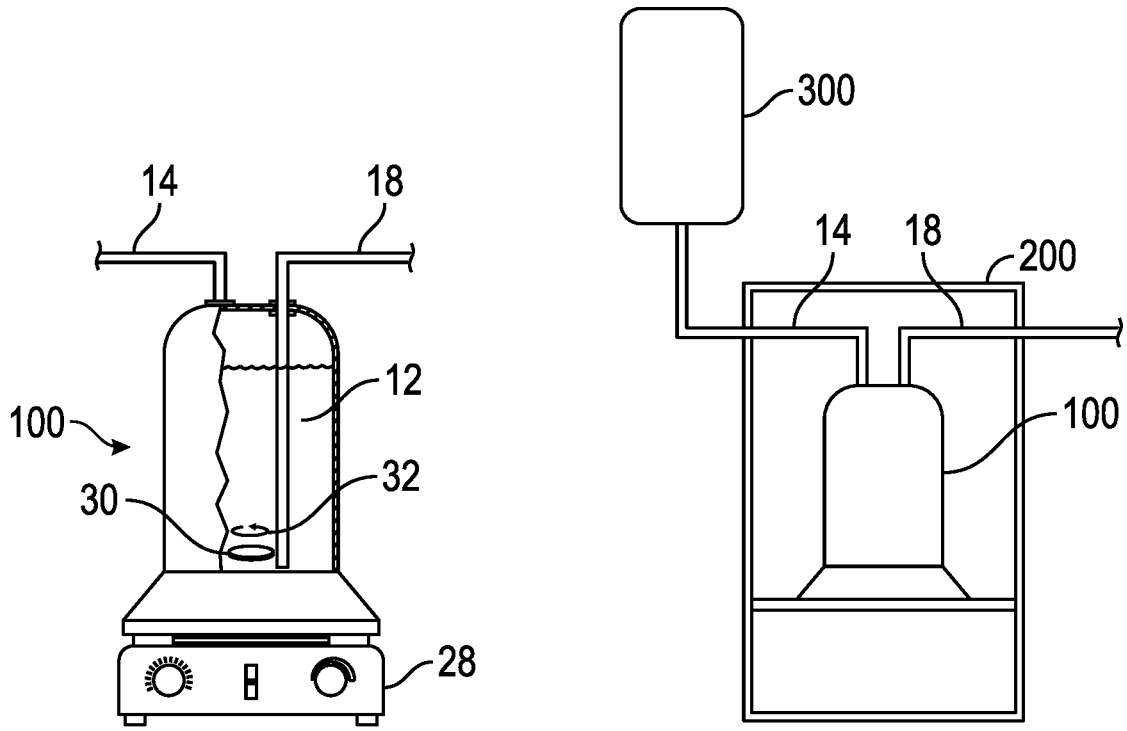
FIG. 2
FIG. 3

SYSTEM AND METHOD FOR FOWL VACCINATION

CROSS-REFERENCE TO RELATED APPLICATIONS

This application is the 35 U.S.C. § 371 national stage of PCT application having serial number PCT/US2015/067223, filed on Dec. 21, 2015. This application also claims priority to U.S. provisional application having serial number 62/095,495 filed on Dec. 22, 2014, which are entirely incorporated herein by reference.

BACKGROUND

In the commercial poultry industry, poultry need constant protection from viruses and bacteria that infect and cause clinical disease. Spray vaccination of young fowl is a relatively inexpensive and long-standing practice, e.g., by delivery of a 7-21 mL aqueous composition onto a moving tray of fowl. The standard delivery mechanism is by syringe injection of the composition into a tube that leads to a nozzle directed toward the fowl in the tray. Multiple vaccine types are administered by spray, but live-attenuated viruses are most common and administered to all commercial poultry produced. Live vaccines are, however, susceptible to inactivation from heat and destruction from pressure gradients in traditional syringe-based vaccine delivery, e.g., through pressure nozzles. Furthermore, applying an aqueous composition by spray is difficult when using a syringe-based delivery system because the speed of the tray moving through the spray and the volume of spray used are dependent on the amount of time it takes the syringe to fully depress and expel all of the aqueous composition. The only way to affect this timing issue is to adjust the air pressure used to depress the syringes, which can lead to further destruction of the virus if the pressure is increased or inappropriate nebulization if the pressure is decreased. In either scenario, the factors can work to prevent all fowl from being properly exposed before the preset volume of aqueous composition is exhausted. Therefore, there is a need for delivery of vaccines, e.g., live vaccines, at a target concentration without substantial risk of degradation of vaccine titer during vaccination.

Moreover, there is a need for a fowl vaccination system and method that delivers an aqueous composition at a constant temperature, pressure and flow rate and for a time duration dictated by tray speed. In the poultry industry, speed of processing is critical to production and profit. Conveyor belt speeds moving the tray of fowl, e.g. chickens, through the vaccination agent spray remains constant to match the processing capabilities of a hatchery and line speed needed to efficiently vaccinate the number of chicks produced per day. It has been shown that increasing the volume of a vaccination agent to fowl increases the efficacy of the vaccine. With current state of the art, it is only possible to maintain the correct line speed and increase volume by reducing pressure and increasing the number of syringes and nozzles used to apply a vaccination agent to chicks. Furthermore, using the syringe based system, line speed and volume can not be mathematically calculated; they are dependent on each other and the time it takes to depress the syringe.

BRIEF SUMMARY

The presently disclosed embodiments, as well as features and aspects thereof, are directed towards a method for vaccinating fowl in need thereof which includes wetting a population of fowl with an effective amount of an aqueous composition comprising a vaccination agent, wherein the aqueous composition is applied at a temperature sufficient to maintain an infective concentration of the vaccination agent during wetting.

In another aspect, the present disclosure is also directed towards an apparatus for applying an effective amount of a vaccination agent to a population of fowl comprising a refrigerated vessel configured to contain a pressurized aqueous vaccination composition; a delivery outlet configured to provide fluid communication between the vessel and a valve; and a nozzle in fluid communication with the valve such that when the valve is actuated, the composition is applied to the population of fowl.

In another aspect, the present disclosure is also directed toward a system for applying a vaccination composition to a population of fowl contained in a carrier tray, e.g., day-old chickens, comprising an apparatus for applying an effective amount of the vaccination agent to a population of fowl comprising a refrigerated vessel configured to contain a pressurized aqueous vaccination composition; a delivery outlet configured to provide fluid communication between the vessel and a valve; and a nozzle in fluid communication with the valve such that when the valve is actuated, the composition is applied to the population of fowl; an application hood defining an application space; an actuation detector in electronic communication with the valve and proximate the application space; and wherein the nozzle is positioned within the hood such that the composition is applied within the application space; and a conveyor configured to transport a population of day-old chickens in a carrier tray on a defined path through the application space and in proximity to the actuation detector such that upon the carrier tray passing in proximity to the actuation detector the valve is actuated; and when the carrier tray is transported along the path beyond the actuation detector, the valve is closed. With the system described herein, an operator may maintain a constant pressure and line speed while changing the volume. This is effected by changing the nozzle used to nebulize the vaccination agent composition. Using the system described herein, the operator may calculate flow rate and volume to be used with a constant line speed and constant pressure.

BRIEF DESCRIPTION OF THE SEVERAL VIEWS OF THE DRAWINGS

In the Figures, like reference numerals refer to like parts throughout the various views unless otherwise indicated. For reference numerals with letter character designations such as "102A" or "102B", the letter character designations may differentiate two like parts or elements present in the same Figure. Letter character designations for reference numerals may be omitted when it is intended that a reference numeral to encompass all parts having the same reference numeral in all Figures.

FIG. 1 is a partial sectional view of an apparatus for applying a composition from a pressurized vessel through a valve and nozzle.

FIG. 2 is a partial sectional view of the apparatus of FIG. 1 with a magnetic stir bar contained in the pressurized vessel and wherein a magnetic stirrer is in magnetic communication with the stir bar.

FIG. 3 is a schematic of the apparatus of FIG. 1 within a refrigeration unit.

DETAILED DESCRIPTION

Figure 4:
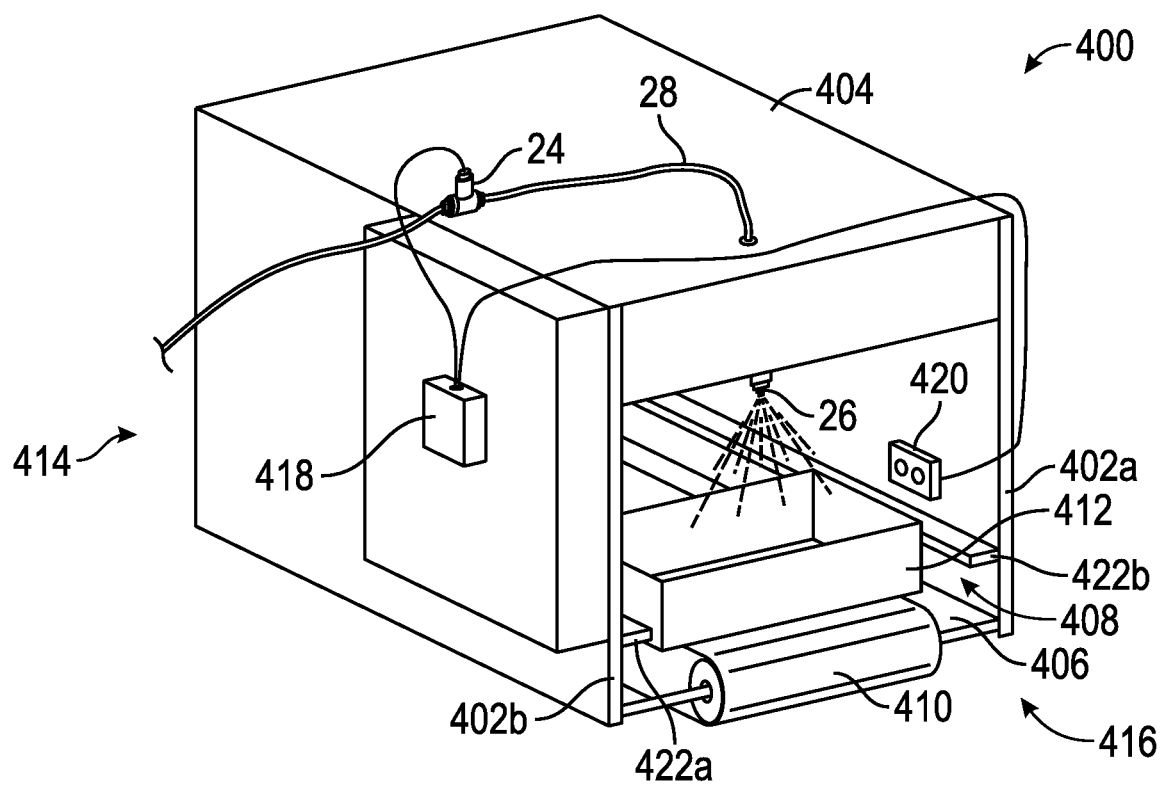
FIG. 4 is a perspective view of an application hood and conveyor system to apply a composition to a population of fowl.

Aspects, features and advantages of several exemplary embodiments of the present invention will become better understood with regard to the following description in connection with the accompanying drawing(s). It should be apparent to those skilled in the art that the described embodiments of the present invention provided herein are illustrative only and not limiting, having been presented by way of example only. All features disclosed in this description may be replaced by alternative features serving the same or similar purpose, unless expressly stated otherwise. Therefore, numerous other embodiments of the modifications thereof are contemplated as falling within the scope of the present invention as defined herein and equivalents thereto. Hence, use of absolute terms such as, for example, "will," "will not," "shall," "shall not," "must" and "must not" are not meant to limit the scope of the present invention as the embodiments disclosed herein are merely exemplary. The word "exemplary" is used herein to mean "serving as an example, instance, or illustration." Any aspect described herein as "exemplary" is not necessarily to be construed as exclusive, preferred or advantageous over other aspects.

The presently disclosed embodiments, as well as features and aspects thereof, are directed towards a method for vaccinating fowl in need thereof which includes wetting a population of fowl with an effective amount of an aqueous composition comprising a vaccination agent, wherein the aqueous composition is applied at a temperature sufficient to maintain an infective concentration of the vaccination agent during wetting.

The word "fowl" means chickens, turkeys, ducks, geese, quail, squab, or guineafowl, although it is envisioned that embodiments of the solutions disclosed herein may be useful for delivery of aqueous compositions to target populations other than fowl. The fowl may be of any developmental stage. In an embodiment, the fowl are from 1 to 20 days old, 1 to 10 days old, or from 1 to 5 days old, or from 1 to 2 days old, or 1 day old (day of hatch).

In an embodiment, the aqueous composition comprises water, or distilled water, or water sufficiently free of active chlorine, hypochlorite ions, or other biologically destructive agents such as bactericides, fungicides, and the like. The aqueous composition may also comprise veterinary-acceptable additives and excipients, such as surfactants, stabilizers, anti-foaming agents, phosphate buffered saline (PBS) or other additives known to the person of ordinary skill in the art.

In an embodiment, the vaccination agent may be a live vaccination agent. The term "live" means living. Examples of a living vaccination agent include live viruses, live bacteria, and live parasites. Examples of a live vaccination agent include ARTVAX, COCCIVAC-B, COCCIVAC-D2, COCCIVAC-T, COCCIVAC-B52, COMBOVAC-3D, ENTEROVAX, INNOVAX-ILT, INNOVAX-ND-SB, LT-IVAX, Mildvac Ma5, MILDVAC®-MASS+ARK, MILDVAC®-MASS+CONN, MILDVAC-GA-98, M-NINEVAX-C, and NEWCASTLE N-63, all of which are available from Merck Animal Health, 556 Morris Avenue, Summit, N.J. 07901, accessible at http://www.merck-animal-health-usa-.com/species/poultry/products.aspx Live vaccination agents also include BUR-CELL®, TROVAC®-NDV, VAXXI-TEK® HVT+IBD, HATCHPAK® COCCI III, BURSA-BLEN® M, IBD-BLEN®, LT-BLEN®, PT-BLEN® (AE/PDX), TREMOR-BLEN®-D (AE), PDX-BLEN®, REOGUARD® L, available from Merial Ltd., 3239 Satellite Blvd., Building 500, Duluth, Ga. 30096USA, accessible at http://avian.merial.us/PoultryProducts/Pages/default.aspx.

Live vaccination agents also include: Poulvac® vaccines designed to immunize against one or more of the following diseases: Marek's disease, Newcastle disease, *Salmonella*, Infectious Bronchitis and Infectious Bursal disease; Inovocox®EM1 vaccines designed to immunize against one or more of *Eimeria tenella, E. acervulina* and *E. maxima* strains, the most common coccidia that affect commercial broilers. These are available from Zoetis, 100 Campus Drive, Floram Park, N.J. 07932, accessible at http://www.zoetis.com/poultry. Live vaccination agents also include: VECTORMUNE® vaccines available from CEVA Poultry Vaccines, 8906 Rosehill Road, Lenexa, Kans. 66215, accessible at http://www.ceva.us/Poultry. Such vaccines are designed to immunize against one or more of the following diseases: Newcastle Disease, Marek's Disease, Fowl Pox, Infectious Bursal Disease, Avian Influenza, Avian Encephalomyelitis and *Mycoplasma*. Commercially available CEVA vaccines include TRANSMUNE® IBD is a poultry vaccine against infectious bursal disease virus, LAYERMUNE® SE is a poultry vaccine against *Salmonella*, CEVAC CORYMUNE® RANGE is a broad spectrum vaccine against infectious coryza and *Salmonella enteritidis*. CEVAC® IBIRD, CEVAC® IBD L, CORYMUNE 4 K®, CORYMUNE 7 K®, LAYERMUNE®, CEVAC VITABRON L, CEVAC® BROILER ND K, CIRCOMUNE and CEVAC FLU-KEM®. Another live vaccination agent includes ADVENT® a coccidiosis vaccine from NOVUS Novus International, Inc.•20 Research Park Dr.•St. Charles, Mo. 63304 and accessible at http://www.novusint.com. Autogenous vaccines (either live or killed) developed against regional disease agents are also included.

In an embodiment, the vaccination agent is sufficient to confer immunity against one or more diseases. The vaccination agent may be a killed, live, or live-attenuated virus, bacterium, or parasite so that the vaccination agent will elicit a sufficient immune response from the fowl but remain biologically innocuous when compared to the original pathogenic form of the infective agent. The term "killed" means no longer living, e.g., no longer able to infect and cause clinical disease but still able to present antigens to the host and elicit an immune response, "live" means living, e.g., still able to infect and replicate in a host, and "attenuated" means still live but determined to be less pathogenic than the original infective agent. For example, the vaccination agent may be effective to confer immunity against disease agents causing Marek's Disease (MD); Infectious Bronchitis (IB); Avian metapneumovirus (Rhinotracheitis, ART); Laryngotracheitis (LT); Mycoplasmosis; Newcastle Disease (ND); Coccidiosis, Pox diseases, Infectious Bursal Disease (IBD), Chicken Anemia, Avian Influenza (AI), Infectious coryza, Tenosynovitis, Colibacilosis, *Salmonellosis*, Bordetellosis, Fowl Cholera, Nephritis Hepatitis, and other respiratory or enteric viruses, bacteria, and parasites.

Some viruses suitable for delivery to a population via embodiments of the solutions disclosed herein may be in capsid form, recombinant, include a protein coat and/or may be or not be contained within a host cell.

In an embodiment, the disclosed method and apparatus may be used to deliver vaccination agents that may flocculate, precipitate, or be suspended in water. For example, a vaccination agent that is an oocyst or has an oocyst structure may be susceptible to settling.

In an embodiment, the disclosed method and apparatus may be used to deliver vaccination agents that are currently mass applied but not by spray. Examples of these vaccines are Pox vaccines, Infectious Laryngotracheitis vaccines, DNA subunit vaccines, and others.

In an embodiment, the concentration, or titer, of an effective amount of a live or attenuated vaccination agent applied to the fowl is typically from about $10^3$ to about $10^{11}$ infectious units per milliliter (p/mL) of aqueous composition. The concentration may be from about $10^3$ to about $10^{10}$ p/mL, from about $10^3$ to about $10^9$ p/mL, from about $10^3$ to about $10^8$ p/mL, or from about $10^3$ to about $10^7$ p/mL, or from about $10^3$ to about $10^6$ p/mL, or from about $10^4$ to about $10^6$ p/mL. The term "infectious units" means a virion or a portion thereof, a protein or portion thereof, a cell or portion thereof, an oocyst or a portion thereof, a linear nucleic acid sequence, or a plasmid. In an embodiment, the titer of live vaccination agent may be measured in "infectious units" and then the live vaccination may be killed. In an embodiment, the titer of a dead or killed vaccination agent may be measured in "antigenic units," e.g., the number of mg protein or mg of nucleic acid per mL. The concentration may be from about 0.1 mg/ml to about 1000 mg/ml, or from about 1 mg. to about 500 mg·L, or from about 10 mg/L to about 250 mg/L.

In an embodiment, the temperature of the aqueous composition may be about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 degrees Celsius (° C.) or a range from a first temperature to a second temperature in the preceding list of integers. For example, the temperature of the aqueous composition may be from about 4° C. to about 10° C. In an embodiment, the temperature of the aqueous composition varies from about 2° C., or about from 2° C. to about 4° C., or from about 2° C. to about 6° C., or from about 2° C. to about 8° C. during a time the method is effected.

In an embodiment, the volume of composition to wet the population of fowl may be 3, 4, 5, 6, 7, 8, 9, 10, 11, 12, 13, 14, 15, 16, 17, 18, 19, 20, 21, 22, 23, 24, 25, 26, 27, 28, 29, or 30 mL, or a range from a first volume to a second volume in the preceding list of integers. For example, the volume of the composition may be from about 5 mL to about 10 mL. For example, a population of fowl may be about 50, 60, 70, 80, 90, 100, 110, 120, 130, 140 or 150 individuals, or a range from a first population to a second population in the preceding list of integers. For example, the population of fowl to which the composition may be applied may be from about 90 to about 100 individuals.

In another aspect, the present disclosure is also directed towards an apparatus for applying an effective amount of a vaccination agent to a population of fowl comprising a refrigerated vessel configured to contain a pressurized aqueous vaccination composition; a delivery outlet configured to provide fluid communication between the vessel and a valve; and a nozzle in fluid communication with the valve such that when the valve is actuated, the composition is applied to the population of fowl at a substantially constant pressure and flow rate and for a duration of time that is a function of the speed at which the population of fowl passes by the nozzle.

The refrigerated vessel may be of any construction, and configured to hold about 10, 20, 30, 40, 50, 60, 70, 80, 90, or 100 pounds per square inch (psi) of internal pressure, or a range of pressures from a first pressure to a second pressure in the preceding list of integers. For example, the pressure may be from about 90 psi to about 100 psi. With reference to FIG. 1, vessel 100 comprises housing 10 that holds the aqueous composition 12 Typically, the vessel holds from about 1 to about 100 liters, or from about 4 to about 100 liters, or from about 1 to about 40 liters, or from about 1 to about 20 liters, or from about 1 to about 10 liters, or from about 1 to about 4 liters. Housing 10 is configured to receive an external pressurized gas, e.g., air, or an inert gas such as nitrogen, or a mixture of air and an inert gas. Gas inlet tube 14 is joined to housing 10 at joint 16. Outlet tube 18 is joined to housing 10 at joint 20 and extends toward internal bottom 22 of vessel 100. Outlet tube 18 is in fluid communication with valve 24, e.g., a solenoid valve or an automated ball valve, that when actuated allows pressurized composition 12 to be urged toward nozzle 26, e.g., through tube 28. Valve 24 may be placed as close to nozzle 26 as possible to minimize the connection between them, e.g., tube 28.

In an embodiment, the nozzle 26 is configured or selected and/or the pressure selected to provide a spray comprising droplets of average diameter of from about 150 μm (micrometers) to about 500 μm; or from about 150 μm to about 400 μm; or from about 200 μm to about 400 μm; or from about 250 μm to about 350 μm; or about 300 μm. In another embodiment, there may be a distribution of droplet diameters in a volume of spray. For example, from about 50% to about 98%; or about 50% to about 90%, or about 50% to about 80%, or from about 50% to about 70% of the droplet diameters may fall in one or more of the above diameter ranges.

The nozzle may have an aperture of from 0.011 to 0.203 inches. For example, the Unijet® nozzles in Table 3 may fall within this range may be utilized according to this disclosure.

In an embodiment, with reference to FIG. 2, the composition 12 may be agitated in vessel 100. For example, magnetic stir bar 30 is in magnetic communication with magnetic stirring plate 28 such that when stirring plate 28 is turned on, magnetic stir bar 30 rotates in direction 32 thus causing agitation, or rotation of composition 12. In this manner, the vaccination agent particles in composition 12 are substantially uniformly distributed in the volume of composition 12. Agitation may alternatively be effected by agitating vessel 100 itself, or by, e.g., use of a rod and paddle agitator inside vessel 100.

In an embodiment, to maintain an appropriate composition temperature, the composition is refrigerated. For example, with reference to FIG. 3, vessel 100 may be enclosed in a refrigeration unit 200. Inlet tube 14 and outlet tube 18 extend from vessel 100 to the outside of unit 200. In this manner, a pressurized gas source 300 may be conveniently connected to inlet tube 14, and the vessel 100 pressurized and readied for use.

In an embodiment, there is disclosed a kit comprising a sterilizable pressure vessel, e.g., vessel 100, sufficient to contain a pressurized aqueous vaccination composition, optionally a magnetic stir bar contained within the vessel, and optionally a stirring plate or external stirring magnet in magnetic communication with the magnetic stir bar. Sterilization of the pressure vessel is generally by high temperature and high-pressure steam, also known by the process of autoclaving. Thus the pressure vessel is autoclavable.

In an embodiment, there is disclosed a kit comprising a sealable, sterilizable, pressure vessel, e.g., vessel 100, distilled or purified water of a selected volume contained by the vessel, and a vaccine inlet configured to receive one or more aliquots of vaccination agent.

In an embodiment, there is disclosed a kit comprising a refrigeration unit, pressure vessel, and optional magnetic stir bar contained within the vessel, and optional stirring plate or external stirring magnet in magnetic communication with the magnetic stir bar. The kit optionally comprises inlet and outlet tubing extending outside the refrigeration unit from the vessel.

In another aspect, the present disclosure is also directed toward a system for applying a vaccination composition to a population of fowl, e.g., 1-5 day-old chickens, comprising an apparatus for applying an effective amount of the vaccination agent to the population of fowl comprising a refrigerated vessel configured to contain a pressurized aqueous vaccination composition; a delivery outlet configured to provide fluid communication between the vessel and a valve; and a nozzle in fluid communication with the valve such that when the valve is actuated, the composition is applied to the population of fowl via the nozzle; an application hood defining an application space; an actuation detector in electronic communication with the valve and proximate the application area; and wherein the nozzle is positioned within the hood such that the composition is applied within the application space; and a conveyor configured to transport a population of 1-5 day-old chickens in a carrier tray on a defined path through the application space and in proximity to the actuation detector such that upon the carrier tray passing in proximity to the actuation detector the valve is actuated open; and when the population is transported along the path in the carrier tray beyond the actuation detector, the valve is closed.

With reference to FIG. 4, application hood 400 comprises vertical walls 402a and 402b, ceiling 404, and floor 406. In this manner, walls 402a, 402b, ceiling 404, and floor 406 define application space 408. Conveyor 410, mounted on application hood 400, moves box 412 (i.e., a carrier tray) from hood entrance 414 through application space 408 and out hood exit 416. Nozzle 26 is mounted on the lower facing surface of ceiling 404 and as such is directed to apply composition 12 on individuals in box 412 as they pass through application space 408. The defined path of box movement may be confined by guides 422a and 422b that are mounted inside the hood, e.g., on walls 402b and 402a, respectively.

Valve controller 418 is in electronic communication with valve 24 and controls its operation, as would be understood by one of ordinary skill in the art of process controls. Valve controller 418 is also in electronic communication with the detector 420. Detector 420 is configured to detect the presence of box 412 as conveyor 410 moves box 412 through application space 408 at a given speed. When the detector 420 detects box 412, detector 420 signals valve controller 418 to open valve 24 and thus apply composition 12 to individuals in box 412 from nozzle 26 at a substantially constant pressure and flow rate from pressurized vessel 100 (not shown in FIG. 4). When box 412 passes by detector 420, detector 420 signals controller 418 to close valve 24. In this way, the composition 12 may be delivered to a population at a substantially constant pressure and flow rate and for a duration of time that is a function of the speed at which the box 412 passes by the nozzle. Notably, a population of fowl may be continuously fed into an application space of an embodiment of the solution. The box 412 for any given embodiment may be as capacious as needed. Advantageously, the valve 24 may stay open as long as needed to apply liquid composition to the fowl passing by the detector.

In an embodiment, a pressure vessel, e.g., 100 in FIG. 1, may be autoclaved and filled with purified, e.g., distilled water and sealed thereafter. The seal may be effected by any method known to those of skill in the art. The vessel may be refrigerated to lower the water to a desired temperature. One or more vaccine agent aliquots, e.g., sealed ampoules, may be diluted into the water and agitated to obtain a substantially uniform distribution of vaccine agent in the water. The vessel, water, and vaccine may then be pressurized and sprayed on a population of fowl according to the description. In an embodiment, the population of fowl may be vaccinated at an unexpectedly higher rate with less total volume of vaccination agent composition compared to the syringe-based method.

In another embodiment, the composition may be refrigerated after exiting the vessel. For example, with reference to FIG. 1, FIG. 2, FIG. 3, and FIG. 4, outlet tubing 18 and tubing 28 may be insulated to maintain a cold temperature of the composition within the tubings.

It will be appreciated by persons skilled in the art that systems, devices and methods described herein are not limited by what has been particularly shown and described herein above. Additionally, one of ordinary skill in programming is able to write computer code or identify appropriate hardware and/or circuits to implement the disclosure without difficulty based on the description in this specification, for example.

Therefore, disclosure of a particular set of program code instructions, process control logic, "ladder" logic or the like is not considered necessary for an adequate understanding of how to make and use the disclosure. Moreover, disclosure of specific process equipment components is not considered necessary for an adequate understanding of how to make and use the disclosure. In one or more exemplary aspects, the functions described may be implemented via process equipment and controls that include valves, logic controllers, pressure sources, hardware, software, firmware, or any combination thereof. If implemented in software, the functions may be stored on or transmitted as one or more instructions or code on a computer-readable medium.

The following non-limiting examples are exemplary embodiments of the present disclosure.

Comparative Example 1

Figure 5:
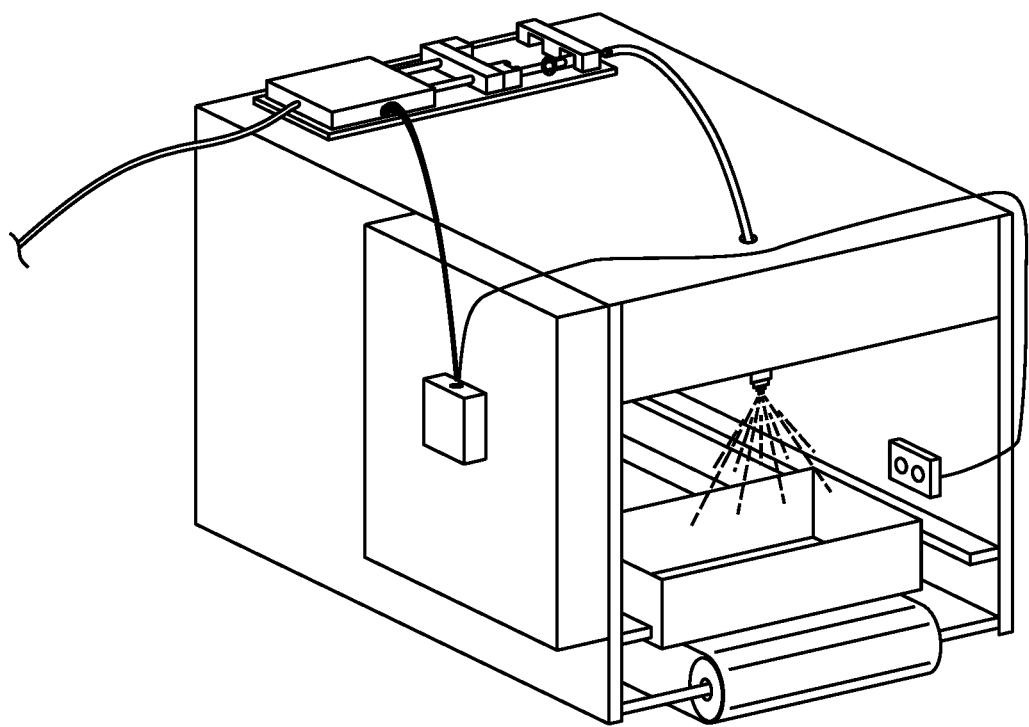
FIG. 5 is a perspective view of a known application hood and conveyor system to apply a composition to a population of fowl using a syringed method.

A rectangular basket configured to hold 100 1-day-old chickens was passed through a generic fowl spray conveyor belt machine used in the poultry industry, e.g., that depicted in FIG. 5, to receive a total volume of 7, 14, and 21 mL of a working solution of an Ark viral vaccine, as shown in Table 1. That is, 7, 14, or 21 mL of working solution was drawn into a plastic syringe and the syringe depressed, by preset timing parameters, to overspray the basket with the drawn volume as the basket passed by the application nozzle. The solution was collected from the corners and middle of the basket. Analysis of the vaccine titer showed about $10^1$ to about $10^2$ p/mL (embryo infectious dose) loss of vaccine titer between the as-collected solution and the working solution, notwithstanding the nozzle aperture and the volume. Results are shown in Table 1.

EXAMPLE 1: Working solutions of Ark virus vaccine was cooled to 4 degrees Celsius in a refrigerator. The working solution was applied to a rectangular basket, configured to hold 100 1-day-old chicks, according to the present disclosure and figures, and the applied solution collected from the corners and middle of the basket. Analysis of the vaccine titer showed about $10^{0.3}$ to $10^{0.6}$ p/mL (embryo infectious dose) loss of vaccine titer between the as-collected solution and the working solution. Results are shown in Table 2.

Therefore, although selected aspects have been illustrated and described in detail, it will be understood that various substitutions and alterations may be made therein without departing from the spirit and scope of the present solution, as defined by the following claims.

TABLE 1

Syringe Based Spray Titrations

| Nozzle | Working Solution | Corner 1 | Corner 2 | Corner 3 | Corner 4 | Middle | Average | Average Loss |
|---|---|---|---|---|---|---|---|---|
| 0033 | $1 \times 10^{5.4}$ | $1 \times 10^{4.2}$ | $1 \times 10^{3.8}$ | $1 \times 10^{4}$ | $1 \times 10^{3.7}$ | N/A | $1 \times 10^{3.9}$ | $1 \times 10^{1.5}$ |
| 0067 | $1 \times 10^{6.2}$ | $1 \times 10^{5.2}$ | $1 \times 10^{6.3}$ | $1 \times 10^{5.3}$ | $1 \times 10^{4.8}$ | $1 \times 10^{4.5}$ | $1 \times 10^{5.2}$ | $1 \times 10^{1}$ |
| 015 | $1 \times 10^{5.5}$ | $1 \times 10^{3.0}$ | $1 \times 10^{3.6}$ | $1 \times 10^{3.6}$ | $1 \times 10^{4.5}$ | $1 \times 10^{3.6}$ | $1 \times 10^{3.7}$ | $1 \times 10^{1.8}$ |

TABLE 2

Constant Pressure Spray Titrations

| Nozzle | Working Solution | Corner 1 | Corner 2 | Corner 3 | Corner 4 | Middle | Average | Average Loss |
|---|---|---|---|---|---|---|---|---|
| 0067 | $1 \times 10^{5.2}$ | $1 \times 10^{5.2}$ | $1 \times 10^{5}$ | $1 \times 10^{4.5}$ | $1 \times 10^{5.3}$ | $1 \times 10^{5.2}$ | $1 \times 10^{4.9}$ | $1 \times 10^{0.3}$ |
| 01 | $1 \times 10^{5.7}$ | $1 \times 10^{4.8}$ | $1 \times 10^{5.5}$ | $1 \times 10^{5}$ | $1 \times 10^{4.6}$ | $1 \times 10^{5.6}$ | $1 \times 10^{5.1}$ | $1 \times 10^{0.6}$ |

TABLE 3

UniJet ® Spray Nozzles, Standard Spray, C Flat Spray nozzles.
Performance data. TPU.

| Spray Angle | Capacity | Equiv. Orifice | Capacity (gallons per minute)* | | | | | | | |
|---|---|---|---|---|---|---|---|---|---|---|
| at 40 psi | Size | Dia. (in.) | 5 | 10 | 20 | 30 | 40 | 60 | 80 | 100 |
| 80° | 0050 | .018 | — | — | .035 | .043 | .050 | .060 | .07 | .08 |
| | 0067 | .021 | — | .033 | .05 | .06 | .067 | .08 | .09 | .11 |
| | 01 | .026 | — | .05 | .07 | .09 | .10 | .12 | .14 | .16 |
| | 015 | .032 | — | .08 | .11 | .13 | .15 | .18 | .21 | .24 |
| | 02 | .035 | .07 | .10 | .14 | .17 | .20 | .24 | .28 | .32 |
| | 03 | .043 | .11 | .15 | .21 | .26 | .30 | .37 | .42 | .47 |
| | 04 | .050 | .14 | .20 | .28 | .35 | .40 | .49 | .57 | .63 |
| | 045 | .053 | .16 | .23 | .32 | .39 | .45 | .55 | .64 | .71 |
| | 05 | .056 | .18 | .25 | .35 | .43 | .50 | .61 | .71 | .79 |
| | 06 | .061 | .21 | .30 | .42 | .52 | .60 | .73 | .85 | .95 |
| | 07 | .066 | .25 | .35 | .49 | .61 | .70 | .86 | .99 | 1.1 |
| | 08 | .071 | .28 | .40 | .57 | .69 | .80 | .98 | 1.1 | 1.3 |
| | 09 | .075 | .32 | .45 | .64 | .78 | .90 | 1.1 | 1.3 | 1.4 |
| | 10 | .079 | .35 | .50 | .71 | .87 | 1.0 | 1.2 | 1.4 | 1.6 |
| | 11 | .083 | .39 | .55 | .78 | .95 | 1.1 | 1.3 | 1.6 | 1.7 |
| | 12 | .087 | .42 | .60 | .85 | 1.0 | 1.2 | 1.5 | 1.7 | 1.9 |
| | 13 | .090 | .46 | .65 | .92 | 1.1 | 1.3 | 1.6 | 1.8 | 2.1 |
| | 14 | .093 | .49 | .70 | .99 | 1.2 | 1.4 | 1.7 | 2.0 | 2.2 |
| | 15 | .097 | .53 | .75 | 1.1 | 1.3 | 1.5 | 1.8 | 2.1 | 2.4 |
| | 16 | .100 | .57 | .80 | 1.1 | 1.4 | 1.6 | 2.0 | 2.3 | 2.5 |
| | 17 | .103 | .60 | .85 | 1.2 | 1.5 | 1.7 | 2.1 | 2.4 | 2.7 |
| | 20 | .112 | .71 | 1.0 | 1.4 | 1.7 | 2.0 | 2.4 | 2.8 | 3.2 |
| | 25 | .121 | .88 | 1.3 | 1.8 | 2.2 | 2.5 | 3.1 | 3.5 | 4.0 |
| | 30 | .133 | 1.1 | 1.5 | 2.1 | 2.6 | 3.0 | 3.7 | 4.2 | 4.7 |
| | 40 | .153 | 1.4 | 2.0 | 2.8 | 3.5 | 4.0 | 4.9 | 5.7 | 6.3 |
| | 50 | .172 | 1.8 | 2.5 | 3.5 | 4.3 | 5.0 | 6.1 | 7.1 | 7.9 |
| | 60 | .188 | 2.1 | 3.0 | 4.2 | 5.2 | 6.0 | 7.3 | 8.5 | 9.5 |
| | 70 | .203 | 2.5 | 3.5 | 4.9 | 6.1 | 7.0 | 8.6 | 9.9 | 11.1 |
| 73° | 0023 | .012 | — | — | .016 | .020 | .023 | .028 | .032 | .036 |
| | 0039 | .016 | — | .020 | .028 | .034 | .039 | .048 | .055 | .062 |
| | 0077 | .023 | — | .039 | .055 | .067 | .077 | .09 | .11 | .12 |
| | 0116 | .028 | .041 | .058 | .082 | .1 | .12 | .14 | .16 | .18 |
| | 0154 | .032 | .054 | .077 | .11 | .13 | .15 | .19 | .22 | .24 |
| | 0231 | .038 | .082 | .12 | .16 | .20 | .23 | .28 | .33 | .37 |
| | 0308 | .044 | .11 | .15 | .22 | .27 | .31 | .38 | .44 | .49 |
| | 0385 | .049 | .14 | .19 | .27 | .33 | .39 | .47 | .54 | .61 |
| | 0462 | .054 | .16 | .23 | .33 | .40 | .46 | .57 | .65 | .73 |

TABLE 3-continued

UniJet ® Spray Nozzles, Standard Spray, C Flat Spray nozzles.
Performance data. TPU.

| | | | | | | | | | |
|---|---|---|---|---|---|---|---|---|---|
| 0616 | .062 | .22 | .31 | .44 | .53 | .62 | .75 | .87 | .97 |
| 0770 | .069 | .27 | .39 | .54 | .67 | .77 | .94 | 1.1 | 1.2 |
| 0924 | .076 | .33 | .46 | .65 | .80 | .92 | 1.1 | 1.3 | 1.5 |

| Spray Angle at 40 psi | Capacity Size | Equiv. Orifice Dia. (in.) | Capacity (gallons per minute)* | | | Spray Angle (°)* | | | |
|---|---|---|---|---|---|---|---|---|---|
| | | | 200 | 300 | 500 | 20 | 40 | 80 | 200 |
| 80° | 0050 | .018 | .11 | .14 | .18 | 61 | 80 | 95 | 101 |
| | 0067 | .021 | .15 | .18 | .24 | 67 | 80 | 94 | 99 |
| | 01 | .026 | .22 | .27 | .35 | 68 | 80 | 89 | 92 |
| | 015 | .032 | .34 | .41 | .53 | 68 | 80 | 89 | 92 |
| | 02 | .035 | .45 | .55 | .71 | 69 | 80 | 88 | 91 |
| | 03 | .043 | .67 | .82 | 1.1 | 70 | 80 | 87 | 90 |
| | 04 | .050 | .89 | 1.1 | 1.4 | 71 | 80 | 86 | 89 |
| | 045 | .053 | 1.0 | 1.2 | 1.6 | 71 | 80 | 86 | 89 |
| | 05 | .056 | 1.1 | 1.4 | 1.8 | 71 | 80 | 86 | 89 |
| | 06 | .061 | 1.3 | 1.6 | 2.1 | 72 | 80 | 85 | 88 |
| | 07 | .066 | 1.6 | 1.9 | 2.5 | 72 | 80 | 85 | 88 |
| | 08 | .071 | 1.8 | 2.2 | 2.8 | 72 | 80 | 84 | 87 |
| | 09 | .075 | 2.0 | 2.5 | 3.2 | 73 | 73 | 73 | 73 |
| | 10 | .079 | 2.2 | 2.7 | 3.5 | 73 | 80 | 84 | 87 |
| | 11 | .083 | 2.5 | 3.0 | 3.9 | 73 | 73 | 73 | 73 |
| | 12 | .087 | 2.7 | 3.3 | 4.2 | 73 | 73 | 73 | 73 |
| | 13 | .090 | 2.9 | 3.6 | 4.6 | 73 | 73 | 73 | 73 |
| | 14 | .093 | 3.1 | 3.8 | 4.9 | 73 | 73 | 73 | 73 |
| | 15 | .097 | 3.4 | 4.1 | 5.3 | 74 | 80 | 83 | 86 |
| | 16 | .100 | 3.6 | 4.4 | 5.7 | 74 | 80 | 83 | 86 |
| | 17 | .103 | 3.8 | 4.7 | 6.0 | 74 | 80 | 83 | 86 |
| | 20 | .112 | 4.5 | 5.5 | 7.1 | 74 | 80 | 83 | 86 |
| | 25 | .121 | 5.6 | 6.8 | 8.8 | 74 | 80 | 83 | 86 |
| | 30 | .133 | 6.7 | 8.2 | 10.6 | 74 | 80 | 83 | 86 |
| | 40 | .153 | 8.9 | 11.0 | 14.1 | 74 | 80 | 83 | 86 |
| | 50 | .172 | 11.2 | 13.7 | 17.7 | 74 | 80 | 83 | 85 |
| | 60 | .188 | 13.4 | 16.4 | 21 | 75 | 80 | 83 | 85 |
| | 70 | .203 | 15.7 | 19.2 | 25 | 75 | 80 | 83 | 86 |
| 73° | 0023 | .012 | .051 | .063 | .081 | 50 | 73 | 89 | 97 |
| | 0039 | .016 | .087 | .11 | .14 | 53 | 73 | 87 | 93 |
| | 0077 | .023 | .17 | .21 | .27 | 53 | 73 | 86 | 92 |
| | 0116 | .028 | .26 | .32 | .41 | 54 | 73 | 85 | 90 |
| | 0154 | .032 | .34 | .42 | .54 | 55 | 73 | 84 | 88 |
| | 0231 | .038 | .52 | .63 | .82 | 56 | 73 | 83 | 87 |
| | 0308 | .044 | .69 | .84 | 1.1 | 58 | 73 | 82 | 86 |
| | 0385 | .049 | .86 | 1.1 | 1.4 | 59 | 73 | 81 | 85 |
| | 0462 | .054 | 1.0 | 1.3 | 1.6 | 60 | 73 | 80 | 84 |
| | 0616 | .062 | 1.4 | 1.7 | 2.2 | 63 | 73 | 79 | 83 |
| | 0770 | .069 | 1.7 | 2.1 | 2.7 | 64 | 73 | 77 | 82 |
| | 0924 | .076 | 2.1 | 2.5 | 3.3 | 65 | 73 | 77 | 80 |

*at the stated pressure in psi.

What is claimed is:

1. A method for vaccinating fowl in need thereof comprising wetting a population of fowl with an effective amount of a refrigerated pressurized aqueous composition,
the aqueous composition comprising a vaccination agent wherein the aqueous composition is applied at a substantially constant temperature sufficient to maintain a concentration of the vaccination agent during wetting via a vessel configured to contain a pressurized aqueous vaccination composition;

wherein the population of fowl is continuously transported;

wherein the aqueous composition is applied via a valve at a substantially constant pressure and flow rate and for a duration of time that is a function of a speed at which the population of fowl passes by a nozzle dispersing the aqueous composition;

wherein the nozzle is in fluid communication with the valve, the valve remaining open for a duration of the continuous transport; and wherein the substantially constant pressure is from about 30 psi to about 50 psi.

2. The method of claim 1, wherein the temperature is from 0° C. to 10° C.

3. The method of claim 1, wherein the fowl are chickens.

4. The method of claim 1, wherein the fowl are 1-5 day-old chickens.

5. The method of claim 4, wherein the effective amount of the aqueous composition is from about 5 mL to about 25 mL per 100 1-5 day-old chickens.

6. The method of claim 1, wherein the wetting comprises applying the aqueous composition substantially uniformly over the population.

7. The method of claim 1, comprising at least two vaccination agents.

8. An apparatus for applying an effective amount of a vaccination agent to a population of fowl comprising:

a refrigerated vessel configured to contain a pressurized aqueous vaccination composition maintained at a substantially constant temperature;

a delivery outlet configured to provide fluid communication between the vessel and a valve;

an actuation detector in electronic communication with the valve, wherein the actuation detector is configured to signal a valve controller to open the valve;

a nozzle in fluid communication with the valve such that when the valve is actuated, the composition is applied to the fowl at a substantially constant pressure and flow rate; and wherein the valve remains open during continuous transportation of the fowl.

9. The apparatus of claim 8 further comprising a pressure inlet valve in electronic communication with a valve controller.

10. The apparatus of claim 8 further comprising a fluid agitator in the vessel.

11. The apparatus of claim 8 further comprising refrigeration of the composition from the vessel to the nozzle.

12. A system for applying a vaccination composition to a population of 1-5 day-old chickens comprising:
   a) an apparatus for applying an effective amount of a vaccination agent to a population of fowl comprising a refrigerated vessel configured to contain a pressurized aqueous vaccination composition maintained at a substantially constant temperature and pressure; a delivery outlet configured to provide fluid communication between the vessel and a valve; and a nozzle in fluid communication with the valve such that when the valve is actuated, the composition is applied to the fowl;
   b) an application hood defining an application space; an actuation detector in electronic communication with the valve and proximate the application area; and wherein the nozzle is positioned within the hood such that the composition is applied within the application space;
   c) a conveyor configured to continuously transport a population of 1-5 day-old chickens on a defined path through the application space and in proximity to the actuation detector such that upon passing in proximity to the actuation detector the valve is actuated and remains actuated during transport; and when the population is transported along the path beyond the actuation detector, the valve is closed.

13. A method for applying an aqueous composition to a population of chickens, the method comprising:
   containing a population of chickens in a carrier tray;
   transporting the carrier tray at a substantially constant speed through an application hood;
   determining that the carrier tray has entered an application space defined within the application hood;
   based on determining that the carrier tray has entered the application space, opening a valve, wherein opening the valve causes the aqueous composition to be delivered to a spray nozzle at a substantially constant pressure and flow rate;
   determining that the carrier tray has exited the application space; and
   based on determining that the carrier tray has exited the application space, closing the valve.

14. An apparatus for applying an effective amount of a vaccination agent to a population of fowl comprising:
   a vessel configured to contain a pressurized aqueous vaccination composition;
   a delivery outlet configured to provide fluid communication between the vessel and a valve, wherein the vessel and the delivery outlet are contained within a refrigeration unit maintained at a substantially constant temperature from 0° C. to 10° C.;
   an actuation detector in electronic communication with the valve, wherein the actuation detector is configured to signal a valve controller to open the valve; and
   a nozzle in fluid communication with the valve such that when the valve is actuated, the composition is applied to the fowl at a substantially constant pressure and flow rate.

* * * * *